United States Patent [19]
Bonaldi et al.

[11] Patent Number: 5,616,741
[45] Date of Patent: Apr. 1, 1997

[54] PROCESS FOR THE PREPARATION OF GLYCINE-CONJUGATED BILE ACIDS

[75] Inventors: Antonio Bonaldi, Chiuduno; Egidio Molinari, Longone al Segrino; Aldo Roda, Bologna, all of Italy

[73] Assignee: Erregierre Industria Chimica S.p.A., S. Paolo D'Argon, Italy

[21] Appl. No.: 468,665

[22] Filed: Jun. 6, 1995

Related U.S. Application Data

[60] Division of Ser. No. 364,241, Dec. 27, 1994, which is a continuation-in-part of Ser. No. 32,282, Mar. 17, 1993, abandoned.

[30] Foreign Application Priority Data

Aug. 4, 1992 [IT] Italy .................. MI92A1924

[51] Int. Cl.$^6$ .................. C07J 9/00; C07J 41/00
[52] U.S. Cl. .................................................. 552/554
[58] Field of Search .................................. 552/554

[56] References Cited

FOREIGN PATENT DOCUMENTS

| | | |
|---|---|---|
| 0046523 | 3/1982 | European Pat. Off. . |
| 0400695 | 12/1990 | European Pat. Off. . |
| 51026870 | 3/1976 | Japan . |

OTHER PUBLICATIONS

A.M. Bellini et al., "Antimicrobial activity of cholane compounds Cholic and deoxycholic acids derivatives (Part I)", Eur. J. Med. Chem.—Chim. Ther., vol. 18, 1983, No. 2, pp. 185–190.

J. Goto et al., "Studies on Analysis of Bile Acids. Preparation of 3-Glucuronides of 7- and 12-Oxo Bile Acids", Chem. Pharm. Bull. vol. 3, (1982), pp. 4422–4428

A.F. Hofmann et al., "The biological utility of bile acid conjugation with glycine or taurine", Falk Symposium 40, Advances in Glucuronide Conjugation, pp. 245–264 (1984).

Enciclopedia Della Chimica, vol. II, pp. 420–425, Uses, Edizioni Scientifiche, Florence, 1972.

H. Igimi et al. 'Cholesterol gallstone dissolution in bile: dissolution kinetics of crystalline (anhydrate and monohydrate) cholesterol with chenodeoxycholate, ursodeoxycholate and their glycine and taurine conjugates.', J. Lipid Res., vol. 22, No. 2, 1981, pp. 254–270.

R. Raedsch et al. 'Kinetics of cholesterol gallstone dissolution by glycocheno-, glycoursodeoxycholic acid, end mixtures thereof in vitro.', Z. Gastroenterologie, vol. 19, No. 4, 1981, pp. 159–163.

*Primary Examiner*—Richard L. Raymond
*Attorney, Agent, or Firm*—Oliff & Berridge

[57] ABSTRACT

A process for the preparation of glycine-conjugated bile acids as general formula (I):

$$Y-NH-CH_2-COOH \qquad (I)$$

wherein Y is the acyl radical of a bile acid selected from the group consisting of ursodeoxycholic, chenodeoxycholic, lithocholic, 3α-7β-12α-tri-hydroxycholanic, 3α-7β-dihydroxy-12-ketocholanic, deoxycholic, dehydrocholic, iodeoxycholic, iocholic acids and relative compositions for hepatic insufficiency treatment, containing the abovesaid acids as active ingredients, in continuation with suitable excipients and/or diluents.

12 Claims, No Drawings

PROCESS FOR THE PREPARATION OF GLYCINE-CONJUGATED BILE ACIDS

This is a Division of application Ser. No. 08/364,241 filed Dec. 27, 1994, which in turn is a Continuation-in-Part Application of application Ser. No. 08/032,282 filed Mar. 17, 1993, now abandoned.

1. Field of the Invention

The present invention relates to a process for the preparation of glycine-conjugated bile acids and/or pharmaceutically acceptable salts thereof, and relative therapeutical compositions useful for treating hepatic insufficiency, containing them as active ingredients.

2. Prior Art Disclosure

The amides formed by bile acids with the amino function of the amino acids, glycine and taurine, are known as conjugated bile acids and relative bile salts.

The bile acids secreted by the liver are almost entirely in the conjugated form. For example, glycoursodeoxycholic acid is the major metabolite that is present in high amounts in bile after ursodeoxycholic acid prolonged administration.

The synthesis of bile acids conjugated with taurine and glycine was described by Bergström and Norman (Enciclopedia della Chimica, USES, Firenze, pages 421–426).

According to said procedure, a mixed anhydride was obtained by treating a bile acid salt and tributylamine with ethylchlorocarbonate in dioxane at low temperature. The obtained anhydride was reacted with a glycine or taurine sodium salt aqueous solution to produce the sodium salt of the conjugated acid. However, the product yields and, especially, purity obtained by the aforesaid process are not high.

THE PRESENT INVENTION

It has surprisingly been found that the physicochemical and biological properties of glycine-conjugated bile acids or of their pharmaceutically acceptable salts, of general formula (I):

Y—NH—CH$_2$—COOH    (I)

where Y is the acyl radical of a bile acid selected from the group consisting of ursodeoxycholic, chenodeoxycholic, lithocholic, 3α-7β-12α-tri-hydroxycholanic, 3α-7β-dihydroxy-12-ketocholanic, deoxycholic, dehydrocholic, iodeoxycholic, iocholic acids, are superior to those of bile acids either as are or conjugated with taurine.

Briefly, they show
a higher solubility at the intestine physiological pH,
an improved absorption by the intestine through active and passive mechanisms,
an improved hepatic transport and bile secretion, without being metabolized,
a remarkable hepatoprotective activity, decidedly higher than that of biliary acids as are.

The present invention therefore relates to therapeutic compositions for the treatment of hepatic insufficiency of the qualitative and quantitative alterations of the biligenetic function, for preventing the formation of the cholesterol calculi, for realising the suitable conditions in order to have the dissolution of radiotransparent calculi optionally present and for the treatment of biliary dyspepsias, containing one or more derivatives of general formula (I) as active ingredients, associated with suitable excipients and/or diluents.

Among the quantitative alterations which the compounds according to the present invention, are able to cure we can mention in particular the form of an oversaturated bile in cholesterol.

In particular the compounds of the present invention are able to prevent the formation and to improve the dissolution of radiotransparent calculi of cholesterol of cholecystic type in working cholecystis and of calculi remaining in the choledocus and occurring after operations on the biliary tracts.

The Applicant has also surprisingly found a process for the preparation of conjugated bile acids of general formula (I) that is not adversely affected by the disadvantages inherent in the known process.

Like the process known from literature, the process of the present invention comprises:

a) salifying bile acid of formula (II)

Y—OH    (II)

wherein Y is as defined above, with a tertiary amine of alkyl or heteroaromatic type in an aprotic solvent at a temperature below 20° C. preferably of from 0° to 20° C.;

b) reacting either the mixture obtained in (a) containing the aforesaid bile acid salt or previously isolated salt, with a chloroformate of general formula (III):

Cl—COOR    (III)

where R is selected from the group consisting of C$_1$–C$_5$ alkyl, phenyl, benzyl, at a temperature below 20° C., preferably of from 0° to 20° C., in the presence of an aprotic solvent to give the corresponding mixed anhydride of formula (IV):

Y—O—COOR    (IV)

where Y and R are as defined above.

But, unlike the process known from literature, the process as per the present invention is characterized by the following stages:

c) mixed anhydride (IV) is reacted with a phenol of general formula (v):

where R$^1$ is selected from H and C$_1$–C$_5$ alkyl, C$_2$–C$_5$ acyl and nitro group, at a temperature below 60° C., preferably of from 35° to 60° C., in the presence of an aprotic solvent and of a tertiary amine as per (a) to give the corresponding phenol ester of formula (VI):

where Y and R$^1$ are as defined above;

d) the product is separated by water addition, extraction of phenol ester in a solvent, evaporation and crystallization, followed by an optional recrystallization;

e) phenol ester is treated with an aqueous solution of glycine as such or in the form of an alkaline metal salt or of a tertiary amine of alkyl or heteroaromatic type, at a temperature ranging from 0° C. to 100° C. (ammonolysis) optionally in the presence of a protic solvent;

f) the product is separated by precipitation acidifying the reaction mixture produced in (e) to a pH between 1 and 4, after optional solvent evaporation and relative filtration;

g) the product recovered in (f) is crystallized in a protic or aprotic polar solvent.

The process of the present invention—which envisages the essential stages of producing an intermediate, i.e. phenol ester (VI), and removing same from the reaction mixture by crystallization—permits to obtain the desired product in high yields and in high purity degree.

DETAILED DESCRIPTION OF THE INVENTION

The pharmaceutical compositions containing the derivatives of formula (I) according to the present invention are useful in human therapy for the treatment of the diseases mentioned above.

To attain the desired therapeutic effects, the present derivatives of formula (I) product can be administered by different routes, in particular by the oral or the parenteral route.

Pharmaceutical compositions containing the derivatives of formula (I) according to the present invention can be prepared by admixing the active ingredient with appropriate excipients or diluents according to conventional techniques, such as for instance those referred to in Remington's Pharmaceutical Sciences Handbook, Hack Publishing Co., USA, 18th ed. (1990).

The compositions of the invention may be administered, on average, once or twice a day; however, more frequent administrations may be convenient, at least in some cases, their number depending on the patient's conditions and on the way of administration chosen. For oral administration, the composition may be provided in the solid or liquid form, such as capsules, pills, tablets, powder, solution, suspension or emulsion, and optionally delayed release forms.

A solid dosage unit may be a gelatin capsule, either soft or hard, containing inert lubricants and excipients, such as lactose, saccharose, starch.

The compounds of the invention may also be formulated as tablets using conventional excipients, such as lactose, saccharose, starch, gelatin, alginic acid, stearic acid, magnesium stearate, talc, arabic gum, colloidal silica.

Gastroresistant compositions for oral administration can be prepared by means of known techniques, such as for instance those already known in the art for enteric release of drugs.

For parenteral administration, the compositions according to the present invention can be administered as injectable formulations, either dissolved or suspended in pharmacologically acceptable diluents, in a sterile carrier such as water or an oil, with or without addition of other compounds.

The oils which can be used are vegetable, animal, mineral or synthetic oils, such as peanut oil, soybean oil or mineral oil.

The carriers which may be used for injectable formulations are water, aqueous solutions of mineral salts, aqueous solutions of dextrose or of other sugars, ethanol, glycols, such as propylene glycol or polyethylene glycol.

The glycine-conjugated bile acids of formula (I) can be administered at a dosage preferably comprised between about 3 mk/Kg and 15 mg/Kg of body weight per day by oral route.

Particularly preferred therapeutic compositions according to the present invention are the gastroresistant ones having controlled release of the active ingredient at pH>6, i.e. only in the distal or ileal intestine parts, preferably in time range between 6 and 8 hours.

With a view to securing a single daily administration, said tablets generally contain about 500 mg of the active ingredient of formula (I).

The solvent used in stages (a) and (b) of the process of the present invention may be either an aprotic polar solvent, preferably acetone, ethyl acetate, dioxane, tetrahydrofuran, or an aprotic dipolar solvent, such as dimethylformamide. More preferably, dioxane is used.

The intermediates obtained in stages (a) and (b) may be either isolated or not: in the latter case, which is the preferred one, the solvent used in stage (a) of the process under the invention is the same as that used in stage (b).

The tertiary amines used in stages (a) and (c) to give the bile acid salt and phenol salt, respectively, are preferably selected from triethylamine, tributylamine, and pyridine.

The $C_1$–$C_5$ alkyl chloroformate (III) used in (b) is preferably a methyl or an ethyl chloroformate.

The aprotic solvent used in (c) may be an aprotic polar solvent selected from acetone, ethyl acetate, dioxane, tetrahydrofuran, or an aprotic dipolar solvent, i.e. N,N-dimethylformamide, and more preferably is dioxane.

The solvent used to crystallize the phenol ester (VI), stage (d) of the process of the present invention, is a polar solvent, either protic or aprotic, such as a $C_1$ to $C_4$ alcohol, or an aprotic polar solvent, as for example acetone and acetic acid esters with $C_1$ to $C_4$ alcohols, preferably acetonitrile either alone or mixed with the aforesaid alcohols.

The bases used to obtain the glycine salt in stage (e) of the process of the present invention are selected out of: sodium hydroxide, potassium hydroxide, lithium hydroxide, potassium and sodium carbonate or bicarbonate, as well as the tertiary alkyl amines preferably used in stage (a) for bile acid salt production.

The solvent used in the aforementioned ammonolysis—stage (e) of the process of the present invention—is a polar solvent, such as water either alone or mixed with $C_1$ to $C_4$ alcohol.

Preferably, stage e) is carried out in the presence of secundary butyl alcohol as the protic solvent, used in amounts of from 0.5 to 1.5 parts in volume in respect of the aqueous solution of glycine, at the reflux temperature of the reaction mixture.

The acid used in stage (f) for conjugated raw acid (I) precipitation is a mineral acid, such as hydrochloric, sulphuric, and phosphoric acids, or an organic acid such as acetic acid.

Separation of the products according to stages d) and f) is typically effected at room temperature (at about 15°–30° C.).

The solvent used in stage (g) of the process of the present invention for the conjugated bile acid (I) crystallization is a protic polar solvent, such as an alcohol, and preferably ethanol, isopropanol, sec-butanol, or an aprotic polar solvent, such as acetone, or $C_1$–$C_4$ alcohol acetates and preferably ethyl acetate.

More preferably, sec-butanol is used as the crystallization solvent, and crystallization is carried out on the moist product.

The following examples are reported by way of indication, not of limitation.

EXAMPLE 1

Ursodeoxycholic acid (250 g) was suspended in 1000 ml dioxane and treated with 66 g triethylamine. The mixture was stirred at room temperature for 1 hr. After cooling to 10° C., 70 g ethyl chloroformate was added dropwise at a temperature maintained below 20° C. Once the addition was completed, the mixture was stirred at 15° C.–20° C. for 1 hr, poured into a solution prepared separately by dissolving 150 ml p-hydroxypropiophenone in 500 ml ethyl acetate and 101 g triethylamine and by heating the obtained solution to 35° C.–40° C., which temperature was maintained during the dropwise addition and for one or two more hours.

The addition of deionized water (1000 ml) gave two phases. The organic phase was washed with 500 ml deionized water and evaporated to a thick oil, which was crystallized with 1500 ml acetonitrile by heating and subsequent cooling to 15° C.

The precipitate was separated by filtration and washed thoroughly with acetonitrile.

Drying yielded 300 g ursodeoxycholic acid ester with the following characteristics: crystalline white powder m.p.=88–92° C.

$[\alpha]_D^{20}$=+41.5°.

Ammonolysis: 65 g glycine and 34 g sodium hydroxide were dissolved in 500 ml of deionized water. The solution was added with 280 ml secondary butyl alcohol and 300 g phenol ester obtained as described above.

The solution was refluxed for 5 hrs, cooled to 30° C. Then the product was precipitated by acidification with phosphoric acid to a pH ranging from 2.5 to 3. After cooling to 15° C., filtering and washing with water and sec-butanol, the moist product was crystallized by hot dissolution with sec-butanol, followed by cooling, filtering and washing with sec-butanol.

260 g glycoursodeoxycholic acid with the following characteristics were obtained:

crystalline white powder m.p.=230–233° C.

$[\alpha]_D^{20}$=+54.6° (C.: 2% in methanol)

Titre=99.82%.

EXAMPLE 2

The phenol ester was obtained following the same procedure as per Example 1, but using ethyl acetate instead of dioxane as the reaction solvent for mixed anhydride preparation.

310 g phenol ester with the following characteristics was obtained:

m.p.=89–92° C.

$[\alpha]_D^{20}$=+42.1°.

Ammonolysis was carried out according to the same procedure as per Example 1.

The product was recrystallized by boiling glycoursodeoxycholic acid with ethyl acetate and water, followed by cooling, filtering, washing with water and ethyl acetate, and drying.

265 g glycoursodeoxycholic acid with the following characteristics was obtained:

crystalline white powder m.p.=231.5–232.5° C.

$[\alpha]_D^{20}$=+55° (C.: 2% in methanol)

Titre=99.9%.

By using the same basic procedure and using the solvents, bases, and chloroformates indicated above, the following glycine-conjugated bile acids were obtained: glycochenodeoxycholic, glycolithocholic, glyco-3α-7β-12α-trihydroxycholanic, glyco-3α-7β-dihydroxy-12-ketocholanic, glycodeoxycholic, glycodehydrocholic, glycoiodeoxycholic, glycoiocholic.

Physicochemical Properties of Glycoursodeoxycholic Acid (GUDCA)

GUDCA shows interesting physicochemical properties, e.g.:

A) A moderate detergent capacity, with critical micellar concentration of 12 μM, similar to that of ursodeoxycholic acid (UDCA) and much lower than that of physiological bile acids.

B) An excellent lipophilia: with absorption in the intestine—even through a passive mechanism—by non-ionic diffusion: LogP=2 (protonated form).

C) A high solubility of the ionized form and low pH needed for the protonated form solubilization (6.5 vs. 8.4 of UDCA).

D) pKa of 3.9, i.e. much lower than that of UDCA.

Thanks to the aforesaid properties, the molecule can be solubilized at the pH of the intestine contents and absorbed through a double mechanism, i.e. passive and active. Bioavailability is thus increased.

Great advantages are provided by GUDCA over UDCA and TUDCA (tauroursodeoxycholic acid).

A') UDCA is much less soluble than GUDCA and can be absorbed only at high pH values (8.5) of the intestine contents. This is consistent with UDCA bioavailability (only 50% of the administered dose is absorbed).

A 100% absorption was observed for GUDCA.

B') Compared with TUDCA, a bile acid with low pKa (approx. 1) and hence always in the ionized form at the physiological pH, GUDCA has pKa of 3.9: it follows that it can be readily protonated and absorbed through a passive mechanism. This can make up for saturations or malfunctioning, if any, of the ileal active transport.

Biological Activity

GUDCA is well absorbed by the intestine through a double mechanism, i.e. active and passive, transported to the liver by the portal system and uptaken. It passes rapidly through the liver without being metabolized and is then secreted in the bile with high transport rate and efficiency.

The aforesaid features favour an excellent accumulation and storage in the enterohepatic circle.

Advantages over UDCA

UDCA is absorbed only through a passive mechanism and is uptaken by liver at 50% (GUDCA at 80%).

In the liver, UDCA is to be linked to glycine and taurine to form GUDCA and TUDCA, in which forms only it is secreted in the bile. This requires liver metabolic processes (UDCA activation with CoA), thioester transfer, need of a substrate, e.g. glycine and taurine, limiting the UDCA secretion rates.

Hepatoprotective Activity

GUDCA, administered to rats by intravenous infusion at a dose of 8 μmol/minute/kg of body weight per 1 hour together with TUDCA at the same dose, can prevent the hepatotoxic effects of the latter bile acid.

Normal values of alkaline phosphatase (ALP) and biliary lactate dehydrogenase (LDH) as well as of bile flow and calcium secretion are thereby obtained.

UDCA is far less effective: ALP and LDH are not normalized by UDCA administration at the aforesaid dose.

We claim:

1. A process for the preparation of a glycine-conjugated bile acid of general formula (I):

$$Y-NH-CH_2-COOH \qquad (I)$$

wherein Y is the acyl radical of a bile acid selected from the group consisting of: ursodeoxycholic, chenodeoxycholic, lithocholic, $3\alpha$-$7\beta$-$12\alpha$-tri-hydroxycholanic, $3\alpha$-$7\beta$-dihydroxy-12-ketocholanic, deoxycholic, dehydrocholic, iodeoxycholic and iocholic acids, comprising:

a) salifying bile acid of formula (II)

$$Y-OH \qquad (II)$$

wherein Y is as defined above, with a tertiary amine of alkyl or heteroaromatic type in an aprotic solvent at a temperature below 20° C.;

b) treating the reaction mixture containing the aforesaid bile acid salt, or the previously isolated salt, with a chloroformate of general formula (III):

$$Cl-COOR \qquad (III)$$

where R is selected from the group consisting of $C_1$-$C_5$ alkyl, phenyl, benzyl, at a temperature below 20° C. in the presence of an aprotic solvent to give the corresponding mixed anhydride of formula (IV):

$$Y-O-COOR \qquad (IV)$$

where Y and R are as defined above;

c) reacting the mixed anhydride (IV) with a phenol of general formula (V):

where $R^1$ is selected from H and $C_1$-$C_5$ alkyl, $C_2$-$C_5$ acyl and nitro group, at a temperature below 60° C. in the presence of an aprotic solvent and of a tertiary amine to give the corresponding phenol ester of formula (VI):

d) separating the product by water addition, phenol ester extraction in a solvent, evaporation and crystallization, followed by an optional recrystallization;

e) treating the phenol ester with an aqueous solution of glycine as is or in the form of an alkaline metal salt or of a tertiary amine of an alkyl or heteroaromatic type, at a temperature ranging from 0° C. to 100° C. optionally in the presence of a protic solvent;

f) separating the product, precipitating by acidifying the reaction mixture produced in (e) to a pH between 1 and 4, after optional solvent evaporation and relative filtration;

g) the product recovered in (f) is crystallized in a protic or aprotic polar solvent.

2. The process according to claim 1 wherein the aprotic solvent used in stages (a) and (b) is an aprotic polar solvent selected from acetone, ethyl acetate, dioxane, tetrahydrofuran, or an aprotic dipolar solvent, selected from dimethylformamide.

3. The process according to claim 1 wherein the intermediates obtained in (a) and (b) are not isolated.

4. The process according to claim 1 wherein the tertiary amines used in (a) and (c) to give the bile acid salt and phenol salt, respectively, are selected from triethylamine, tributylamine, and pyridine.

5. The process according to claim 1 wherein $C_1$-$C_5$ alkyl chloroformate (III) used in (b) is methyl or ethyl chloroformate.

6. The process according to claim 1 wherein the aprotic solvent used in (c) is an aprotic polar solvent selected from acetone, ethyl acetate, dioxane, tetrahydrofuran, or an aprotic dipolar solvent, such as N,N-dimethylformamide.

7. The process according to claim 1 wherein the phenol ester crystallization solvent (stage d) is a protic or aprotic polar solvent, preferably acetonitrile either alone or mixed with $C_1$-$C_4$ alcohols.

8. The process according to claim 2 wherein the bases used to obtain the glycine salt employed in stage (e) are selected from: sodium hydroxide, potassium hydroxide, lithium hydroxide, potassium or sodium carbonate or bicarbonate, and the tertiary alkyl amines are selected from triethylamine, tributylamine, and pyridine.

9. The process according to claim 1 wherein the acid used in stage (f) for conjugated raw acid (I) precipitation is a mineral acid, selected from hydrochloric, sulphuric, and phosphoric acids, or an organic acid such as acetic acid.

10. The process according to claim 1 wherein the solvent used for conjugated bile acid (I) crystallization (stage g) is a protic polar solvent consisting of an alcohol or an aprotic polar solvent consisting of acetone or $C_1$-$C_4$ alcohol acetates.

11. The process according to claim 1, wherein stages a) and b) are carried out at a temperature of from 0° to 20°C.; the solvent used in stages a) and b) is dioxane; the aprotic solvent used in stage c) is dioxane; step c) is carried out at a temperature of from 35° to 60° C.; stage e) is carried out in the presence of secondary butyl alcohol as the protic solvent, used in amounts of from 0.5 to 1.5 parts in volume in respect of the amount of the aqueous solution of glycine, at the reflux temperature of the reaction mixture; separation of the products according to stages d) and f) is effected at room temperature; the solvent used in stage g) is sec-butanol, and crystallization is carried out on the moist product.

12. The process according to claim 1, wherein the glycine-conjugated bile acid is glycoursodeoxycholic acid.

* * * * *